United States Patent
Lin

(10) Patent No.: US 8,771,308 B2
(45) Date of Patent: Jul. 8, 2014

(54) TRANSMISSION MECHANISM OF EYEBROW TATTOO MACHINE

(75) Inventor: Su-Lin Lin, Taipei (TW)

(73) Assignee: Mei-Cha-Na Hsinyen Co., Ltd., Taipei (TW)

( * ) Notice: Subject to any disclaimer, the term of this patent is extended or adjusted under 35 U.S.C. 154(b) by 358 days.

(21) Appl. No.: 13/137,089

(22) Filed: Jul. 20, 2011

(65) Prior Publication Data

US 2012/0279330 A1 Nov. 8, 2012

(30) Foreign Application Priority Data

May 6, 2011 (TW) .............................. 100208093 U

(51) Int. Cl.
*A61B 17/34* (2006.01)
*B43K 5/00* (2006.01)

(52) U.S. Cl.
USPC ................................ 606/186; 74/25; 81/9.22

(58) Field of Classification Search
USPC ........... 74/24, 23, 22 A, 22 R, 25, 47, 49, 86; 606/186; 81/9.22; 30/362
See application file for complete search history.

(56) References Cited

U.S. PATENT DOCUMENTS

| | | | |
|---|---|---|---|
| 3,731,545 A * | 5/1973 | Beezer | 74/24 |
| 3,834,652 A * | 9/1974 | Sachs | 242/356.2 |
| 4,031,783 A * | 6/1977 | Paul et al. | 81/9.22 |
| 4,204,438 A * | 5/1980 | Binaris et al. | 81/9.22 |
| 4,437,361 A * | 3/1984 | Steckel et al. | 81/9.22 |
| 4,914,988 A * | 4/1990 | Chang | 81/9.22 |
| 5,279,552 A * | 1/1994 | Magnet | 604/47 |
| 5,471,102 A * | 11/1995 | Becker et al. | 310/50 |
| 5,737,966 A * | 4/1998 | Yoshida | 74/44 |
| 6,033,421 A * | 3/2000 | Theiss et al. | 606/186 |
| 7,207,242 B1 * | 4/2007 | Daigle | 81/9.22 |
| 2003/0195542 A1 * | 10/2003 | Lee | 606/186 |
| 2008/0208235 A1 * | 8/2008 | Ulmer et al. | 606/186 |
| 2009/0209992 A1 * | 8/2009 | McConchie | 606/186 |
| 2010/0191268 A1 * | 7/2010 | Lee | 606/185 |
| 2012/0179186 A1 * | 7/2012 | Abbott | 606/185 |
| 2012/0209307 A1 * | 8/2012 | Snijders | 606/186 |

* cited by examiner

*Primary Examiner* — Justin Krause
*Assistant Examiner* — Gregory Prather
(74) *Attorney, Agent, or Firm* — Bacon & Thomas, PLLC

(57) ABSTRACT

The present invention refers to a transmission mechanism of an eyebrow tattoo machine, which includes an eccentric rotation shaft connected to a driving axle of a motor and having a bottom end configured to rotate eccentrically with respect to the driving axle, an upper bearing coupled with the bottom end of the eccentric rotation shaft, a position-limiting cover longitudinally provided with a position-limiting groove, and a swinging rod element mounted to the upper bearing and provided with a swinging rod and a position-limiting rod on two sides respectively. Since the position-limiting rod is only allowed to swing up and down in the position-limiting groove when the eccentric rotation shaft drives the upper bearing and the swinging rod element, the end of the swinging rod away from the upper bearing can swing up and down and then drive a tattoo needle to move vertically up and down through a lateral bearing.

3 Claims, 4 Drawing Sheets

TRANSMISSION MECHANISM OF EYEBROW TATTOO MACHINE

FIELD OF THE INVENTION

The present invention relates to a transmission mechanism of an eyebrow tattoo machine, which utilizes an upper bearing and a lateral bearing to serve as the major components for transmitting power from a motor to a tattoo needle without getting involved engaging action of plastic components, so as to effectively solve the problem of deformation and loosening of the conventional plastic power transmitting components and significantly increases the service life of the eyebrow tattoo machine.

BACKGROUND OF THE INVENTION

Eyebrow tattooing is a relatively minor cosmetic procedure widely practiced nowadays. Typically, eyebrow tattooing involves the use of a motorized machine which drives a single needle or a group of needles into vertical oscillation and thereby injects a liquid dye preparation into the skin in or around the eyebrow areas, so as to form continuous patches of permanent color markings intended to enhance the appearance of eyebrows.

Generally speaking, a conventional eyebrow tattoo machine consists of a transmission mechanism and a needle mounting mechanism, wherein the transmission mechanism is configured for driving the needle(s) in the needle mounting mechanism into reciprocal up-and-down motion along the central axis of the eyebrow tattoo machine. With such a machine, an eyebrow tattooist can use the pigment-dispensing needle tip(s) to tattoo the desired pattern, designed according to the customer's needs, on the customer's face. Once the eyebrow tattooing procedure is completed, the used needle(s) are removed and replaced by a new one or new ones for subsequent use. The replacement of used tattoo needles is to ensure the safety and sanitation of eyebrow tattooing and prevent the transmission of blood-borne diseases.

Please refer to FIG. 1 for an exploded perspective view of a conventional eyebrow tattoo machine 1. The eyebrow tattoo machine 1 is provided therein with a motor 10. The motor 10 has an eccentric shaft 100 extending outward from one end and is configured to drive the eccentric shaft 100 into eccentric rotation. Also provided in the eyebrow tattoo machine 1 is a transmission mechanism which essentially includes a cover 11, a swinging element 12, and a linking member 13. The cover 11 is penetrated by a receiving space 110 into which the eccentric shaft 100 of the motor 10 extends, and the bottom side of the cover 11 is concavely provided with two axial holes 111. The swinging element 12 is made of plastic and is bilaterally provided with a pair of pivots 120, each received in a corresponding one of the axial holes 111. In addition, the swinging element 12 has an engaging portion 121 at the top end. By virtue of the elasticity of the plastic material of which the swinging element 12 is made, the engaging portion 121 is fixedly engaged with the eccentric shaft 100 through the engaging action of the plastic material.

The bottom end of the swinging element 12 is formed as a swinging portion 122. When the eccentric shaft 100 is rotated eccentrically, the swinging element 12 is driven by the eccentric shaft 100 such that the swinging portion 122 swings longitudinally, i.e., up and down along the axial direction of the eyebrow tattoo machine 1. On the other hand, the top end of the linking member 13 is pivotally connected to the swinging portion 122, and the bottom end of the linking member 13 is connected to a needle (not shown) of the eyebrow tattoo machine 1 by other components. When the eccentric shaft 100 drives the swinging element 12 and thereby drives the swinging portion 122 to swing longitudinally, the linking member 13 is moved up and down with the swinging portion 122 to impart vertical oscillation, which enables the insertion of a liquid dye preparation into the tattooed area. Thus, eyebrow tattooing is carried out.

However, the conventional eyebrow tattoo machine 1 leaves much room for improvement. Referring to FIG. 1, as the swinging element 12 is fixedly engaged with the eccentric shaft 100 by the engaging action of the plastic material of the swinging element 12, the portion of the engaging portion 121 that is adjacent to the eccentric shaft 100 tends to be permanently deformed after the eyebrow tattoo machine 1 is used for a long time. Should it happen, the engaging portion 121 may become loose from the eccentric shaft 100, causing ineffective power transmission from the motor 10 to the swinging element 12. Even worse, the swinging element 12 and the linking member 13 may shake in an undesirable manner, thus shortening the service life of the eyebrow tattoo machine 1 and, in the end, incurring expenses for buying a new eyebrow tattoo machine. Moreover, when the eyebrow tattoo machine 1 is used in an area of relatively high hardness, such as where the eyebrow bone lies, the linking member 13 and the needle connected thereto may be shifted angularly and therefore lead to erroneous operation of the eyebrow tattoo machine 1. Such erroneous operation not only compromises the efficiency of the eyebrow tattooing procedure seriously, but also may cause irremediable defects on customers' faces. While attempts have been made to make the swinging element 12 out of metal as a solution to the aforesaid plastic deformation problem, the metallic swinging element 12 has its own drawbacks. For example, friction with the metallic swinging element 12 tends to generate high heat, and the adjacent components are very likely to deteriorate after long-term exposure to such high heat. As a result, an eyebrow tattoo machine with the metallic swinging element 12 still has a shortened service life, which translates into a monetary burden on the user.

Therefore, the issue to be addressed by the present invention is to overcome the various problems of the transmission mechanism of the conventional eyebrow tattoo machines (e.g., the loosening of deformed plastic parts, the generation of high heat by metallic components, and so on) and design an improved transmission mechanism capable of delivering a vertical actuating force steadily to the tattoo needle(s) to prevent the needle(s) from being shifted angularly.

BRIEF SUMMARY OF THE INVENTION

In view of the aforementioned drawbacks of the transmission mechanism of the conventional eyebrow tattoo machines, the inventor of the present invention conducted extensive research and experiment and finally succeeded in developing an improved transmission mechanism for use in an eyebrow tattoo machine. The transmission mechanism disclosed herein is intended to effectively solve the plastic deformation and heat generation problems in the prior art and increase the service lives of eyebrow tattoo machines.

It is an object of the present invention to provide a transmission mechanism of an eyebrow tattoo machine, wherein the transmission mechanism includes an eccentric rotation shaft, an upper bearing, a position-limiting cover, a swinging rod element, a lateral bearing, and a linking member. The eccentric rotation shaft is connected to the driving axle of a motor, and the bottom end of the eccentric rotation shaft is configured to rotate eccentrically with respect to the driving axle of the motor. The inner periphery of the upper bearing is coupled with the bottom end of the eccentric rotation shaft so as for the eccentric rotation shaft to drive the upper bearing into rotation. The position-limiting cover is longitudinally provided with a position-limiting groove and is located adjacent to the eccentric rotation shaft. The swinging rod element is mounted around and fixed to the outer periphery of the upper bearing and is protrudingly provided with a swinging rod and a position-limiting rod on two sides respectively. The position-limiting rod extends into the position-limiting groove. When the eccentric rotation shaft drives the upper bearing and consequently the swinging rod element, the position-limiting rod is only allowed to swing up and down in the position-limiting groove, thus causing the end of the swinging rod that is away from the upper bearing to swing up and down. The inner periphery of the lateral bearing is coupled with the swinging rod so as for the lateral bearing to be driven to swing up and down by the swinging rod. The linking member is pivotally provided with a pivoting element. The pivoting element is mounted around and fixed to the outer periphery of the lateral bearing so that, when the lateral bearing swings up and down, the pivoting element is driven up and down by the lateral bearing and moves the linking member up an down, thereby causing a tattoo needle or tattoo needles which are connected either directly or indirectly to the linking member to move vertically up and down. Thus, according to the present invention, the upper bearing and the lateral bearing serve as the major components for power transmission, and power transmission does not involve the engaging action of plastic components. This solves the problem of deformation and loosening of the conventional plastic power transmitting components and significantly increases the service life of an eyebrow tattoo machine using the disclosed transmission mechanism.

Another object of the present invention is to provide the foregoing transmission mechanism, wherein the swinging rod is protrudingly provided with a stopper, and the lateral bearing has one side lying against the stopper to prevent unnecessary sliding of the lateral bearing.

Still another object of the present invention is to provide the foregoing transmission mechanism, wherein the position-limiting cover is penetrated by two fastening holes so that the position-limiting cover can be fixed at a position adjacent to the motor by two screws which are inserted through the fastening holes respectively.

Yet another object of the present invention is to provide the foregoing transmission mechanism, wherein the linking member has a fork portion to which the pivoting element is pivotally connected. Thus, when the lateral bearing swings, any transverse displacement of the lateral bearing only causes the pivoting element to rotate about its own pivots, and the force of the transverse displacement is not transmitted to the linking member, so as for the linking member to move vertically up and down.

BRIEF DESCRIPTION OF THE SEVERAL VIEWS OF THE DRAWINGS

The structure as well as a preferred mode of use, further objects, and advantages of the present invention will be best understood by referring to the following detailed description of an illustrative embodiment in conjunction with the accompanying drawings, in which.

DETAILED DESCRIPTION OF THE INVENTION

The inventor of the present invention has long been engaged in the research, development, and manufacture of eyebrow tattoo machines and like cosmetic products. In the process, the inventor has found that the transmission mechanism of the conventional eyebrow tattoo machines is typically configured to transmit power by the engaging action of a plastic component. This engaging action, however, often leads to deformation and loosening of the plastic component, which not only cause operational problems but also shorten the service lives of eyebrow tattoo machines. Although attempts have been made to overcome the aforesaid drawbacks of the prior art by improving the overall structure of the conventional eyebrow tattoo machines, an ideal solution has yet to be found. Therefore, the inventor came up with the idea of applying bearing transmission to the transmission mechanism of an eyebrow tattoo machine. It is hoped that, simply by improving the transmission mechanism, deformation and loosening of the power transmitting components can be effectively prevented to extend the service life, and increase the operational stability, of eyebrow tattoo machines.

Figure 1:
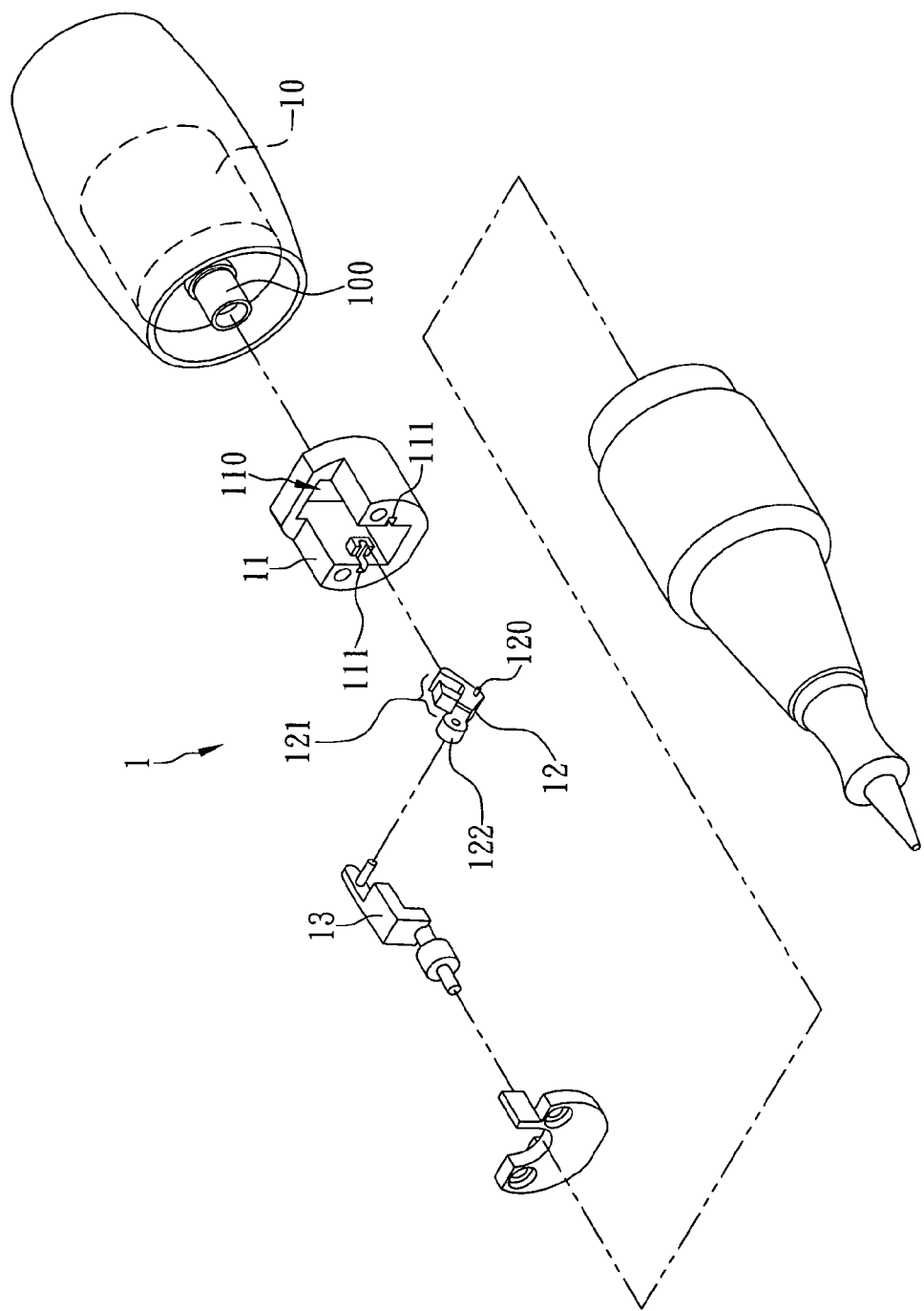
FIG. 1 is an exploded perspective view of a conventional eyebrow tattoo machine.
Figure 2:
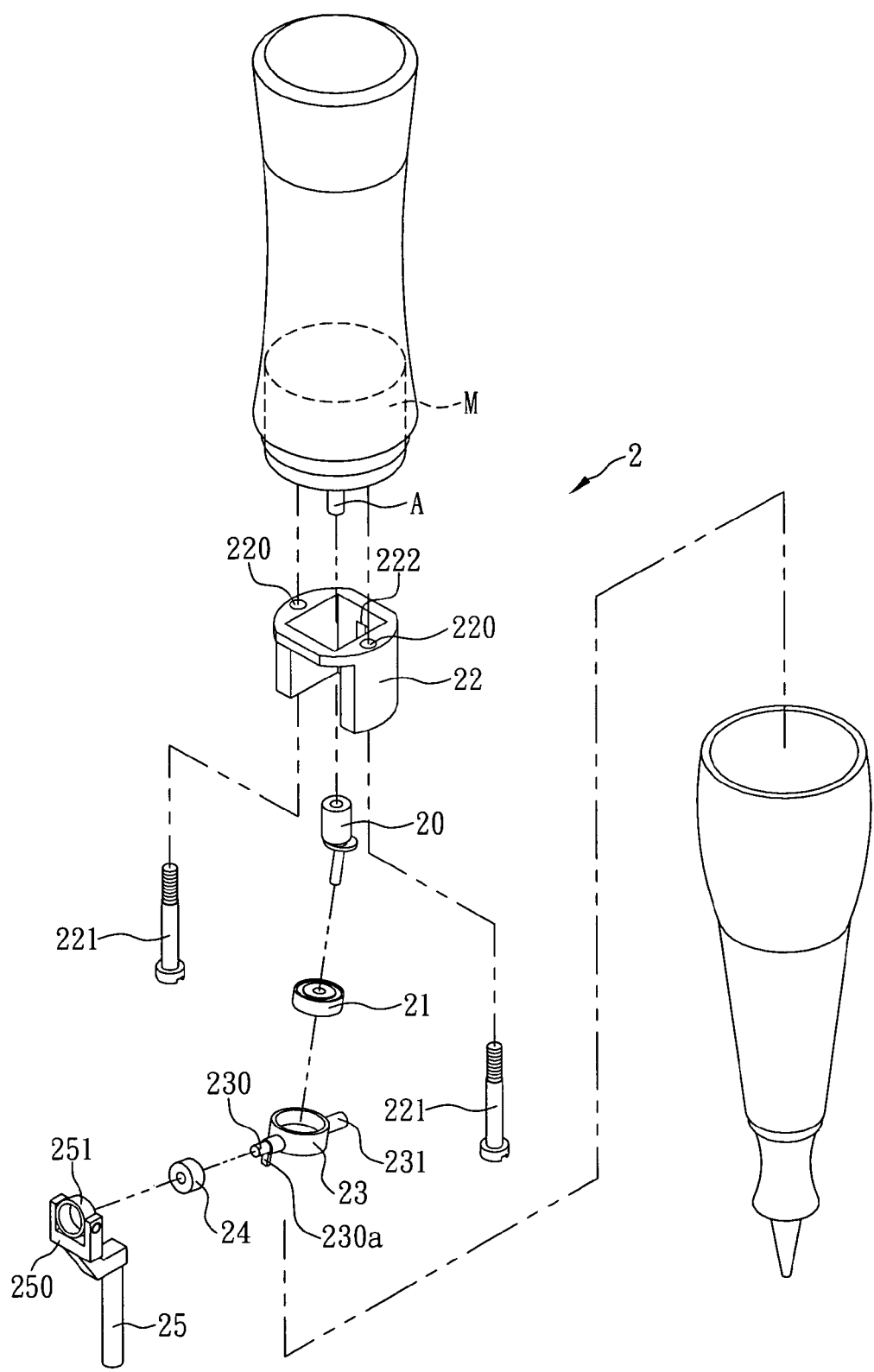
FIG. 2 is an exploded perspective view of a preferred embodiment of the present invention.

The present invention discloses a transmission mechanism for use in an eyebrow tattoo machine. Referring to FIG. 2, a transmission mechanism 2 according to a preferred embodiment of the present invention includes an eccentric rotation shaft 20, an upper bearing 21, a position-limiting cover 22, a swinging rod element 23, a lateral bearing 24, and a linking member 25. The eccentric rotation shaft 20 has a curved configuration and is made of metal. However, the material of the eccentric rotation shaft 20 is not limited to metal; other materials (e.g., plastic) can also be used when making the eccentric rotation shaft 20 of the present invention. All combinations and variations easily conceivable by a person skilled in the art should fall within the scope of the present invention. As shown in FIG. 2, a motor M has a downwardly extending driving axle A, the upper end of the eccentric rotation shaft 20 is connected to the driving axle A of the motor M, and the bottom end of the eccentric rotation shaft 20 is configured to rotate eccentrically with respective to the driving axle A. Due to the curved configuration of the eccentric rotation shaft 20, when the driving axle A is driven to rotate by the motor M, the bottom end of the eccentric rotation shaft 20 is rotated eccentrically with respect to the driving axle A of the motor M.

Figure 3:
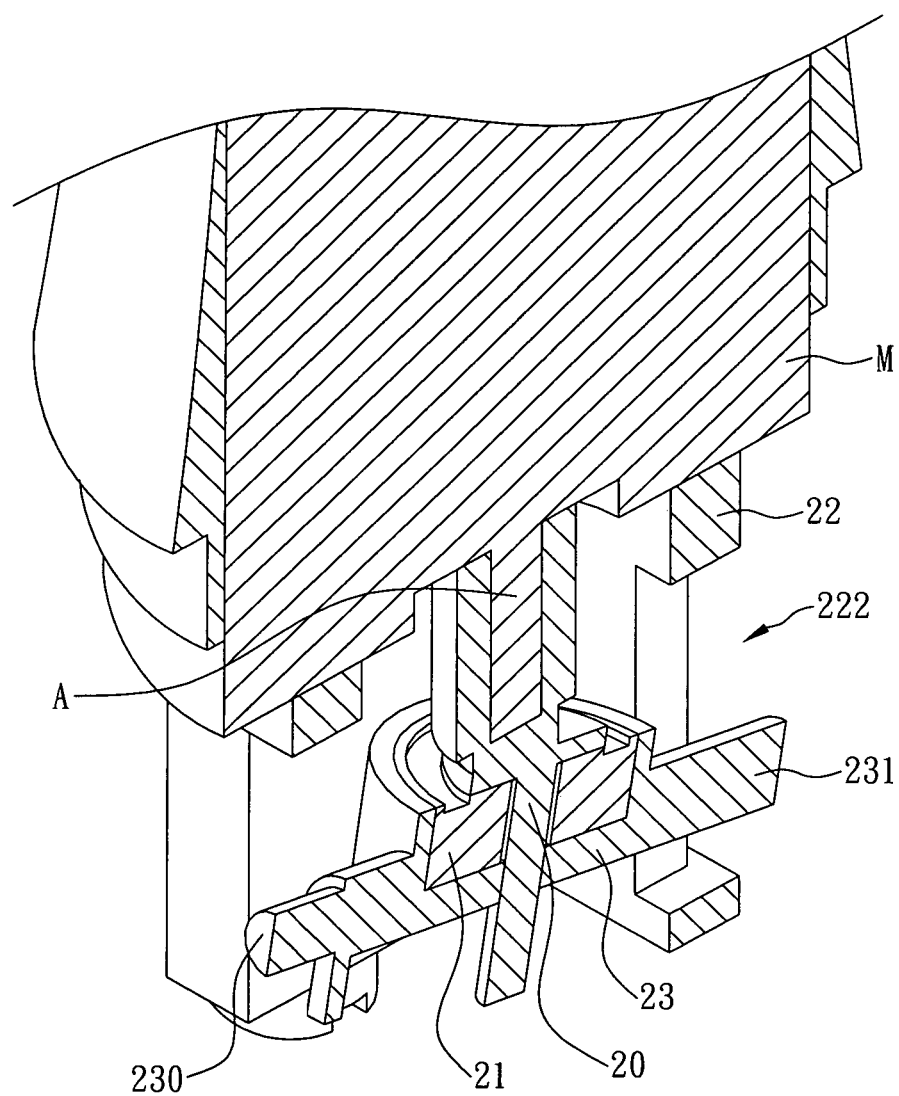
FIG. 3 is a schematic partial sectional view of the preferred embodiment of the present invention.

Referring again to FIG. 2, the inner periphery of the upper bearing 21 is coupled with the bottom end of the eccentric rotation shaft 20 so as for the eccentric rotation shaft 20 to drive the upper bearing 21 into rotation. The position-limiting cover 22 is made of plastic, but the material of the position-limiting cover 22 is not an essential limitation to the present invention and therefore is not limited to plastic. The position-limiting cover 22 has two fastening holes 220 which pass through the position-limiting cover 22. Thus, the position-limiting cover 22 can be secured adjacent to the motor M by two screws 221 inserted respectively through the fastening holes 220. Referring to FIGS. 2 and 3, the position-limiting cover 22 is longitudinally formed with a position-limiting groove 222. As the position-limiting cover 22 is fixed at a position adjacent to the motor M, the position-limiting cover 22 is adjacent to the eccentric rotation shaft 20.

With reference to FIGS. 2 and 3, the swinging rod element 23 is fixedly mounted around the outer periphery of the upper bearing 21. The swinging rod element 23 is protrudingly provided with a swinging rod 230 on one side (the left side in the drawings) and is protrudingly provided with a position-limiting rod 231 on the other side (the right side in the drawings), wherein both the swinging rod 230 and the position-limiting rod 231 have a generally cylindrical shape. As shown in FIG. 3, the position-limiting rod 231 extends into the position-limiting groove 222; therefore, when the eccentric rotation shaft 20 drives the upper bearing 21 and consequently the swinging rod element 23, the position-limiting rod 231 can only swing up and down within the position-limiting groove 222. Likewise, the end of the swinging rod 230 that is away from the upper bearing 21 is only allowed to swing up and down. In other words, the moving directions of the swinging rod 230 are limited by cooperation between the position-limiting groove 222 and the position-limiting rod 231. As a result, the swinging rod 230 is prevented from transverse displacement, and the motion of the swinging rod 230 is reduced almost exclusively to swinging up and down.

Figure 4:
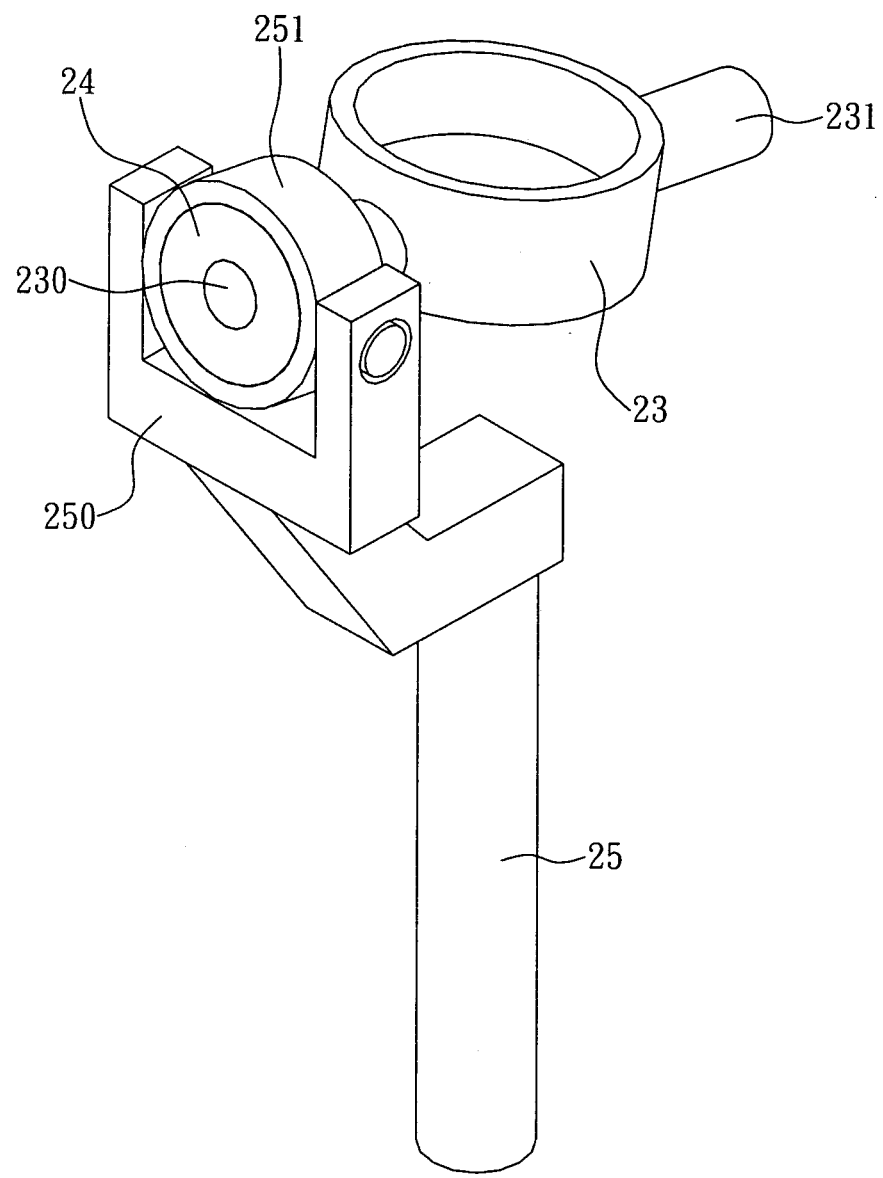
FIG. 4 is an assembled perspective view of a swinging rod, a lateral bearing, and a linking member according to the present invention.

Referring to FIG. 4 in conjunction with FIG. 2, the inner periphery of the lateral bearing 24 is coupled with the swinging rod 230. The swinging rod 230 is protrudingly provided with a stopper 230a, and the lateral bearing 24 has one side lying against the stopper 230a. This is to prevent the lateral bearing 24 from unnecessary sliding. On the other hand, the lateral bearing 24 can be driven by the swinging rod 230 to swing up and down. The linking member 25 has a fork portion 250, and a pivoting element 251 is pivotally connected to the fork portion 250. The pivoting element 251 is fixedly mounted around the outer periphery of the lateral bearing 24 so as for the lateral bearing 24 to drive the pivoting element 251 into up-and-down motion, which in turn causes the linking member 25 to move up and down. It should be pointed out that when the lateral bearing 24 swings vertically, it does not swing along a straight line but has a curvilinear trajectory. As the pivoting element 251 is mounted around the lateral bearing 24 and pivotally connected to the linking member 25, the minor transverse displacement of the swinging lateral bearing 24 only causes the pivoting element 251 to rotate about its own pivots. The force of the transverse displacement will not be transmitted to the linking member 25, but only the longitudinal force will, so as for the linking member 25 to move up and down. Thus, a tattoo needle or tattoo needles (not shown) which are directly or indirectly connected to the linking member 25 are allowed to move vertically up and down with the linking member 25.

In summary, referring to FIG. 2, the present invention uses the upper bearing 21 and the lateral bearing 24 as the major components for power transmission. By doing so, heat generation which may otherwise result from friction is eliminated, and the high heat problems typical of the conventional eyebrow tattoo machines are effectively solved. As the components of the transmission mechanism are safe from deterioration attributable to long-term exposure to high heat, an eyebrow tattoo machine using the present invention may have an extended service life. Furthermore, power transmission according to the present invention does not rely on the engaging action of plastic components. Because of that, the problem of deformation and loosening of the otherwise necessary plastic components is overcome to effectively protect eyebrow tattoo machines from damage; in consequence, the expenses for buying new eyebrow tattoo machines can be saved. Besides, the present invention prevents the tattoo needles from tilting even when the eyebrow tattoo machine is used over a region of relatively high hardness, such as over the eyebrow bone. Thus, operational errors can be avoided, and the efficiency of eyebrow tattooing effectively increased.

While the invention herein disclosed has been described by means of specific embodiments, numerous modifications and variations could be made thereto by those skilled in the art without departing from the scope of the invention set forth in the claims.

What is claimed is:

1. A transmission mechanism of an eyebrow tattoo machine, comprising:
   an eccentric rotation shaft having an upper end connected to a driving axle of a motor and a bottom end configured to rotate eccentrically with respective to the driving axle;
   an upper bearing having an inner periphery coupled with the bottom end of the eccentric rotation shaft so as for the eccentric rotation shaft to drive the upper bearing into rotation;
   a position-limiting cover longitudinally formed with a position-limiting groove and located adjacent to the eccentric rotation shaft;
   a swinging rod element fixedly mounted around an outer periphery of the upper bearing, having a side protrudingly provided with a swinging rod, and having another side protrudingly provided with a position-limiting rod, wherein the position-limiting rod extends into the position-limiting groove such that, when the eccentric rotation shaft drives the upper bearing and thereby drives the swinging rod element, the position-limiting rod can only swing up and down in the position-limiting groove, thereby causing an end of the swinging rod that is away from the upper bearing to swing up and down;
   a lateral bearing having an inner periphery coupled with the swinging rod so as for the swinging rod to drive the lateral bearing into up-and-down swinging motion; and
   a linking member having a fork portion and a pivoting element, wherein the pivoting element is fixedly mounted around an outer periphery of the lateral bearing and pivotally connected to the fork portion such that, when the lateral bearing swings up and down, the pivoting element is driven by the lateral bearing to move up and down, thereby causing the linking member to move up and down.

2. The transmission mechanism of claim 1, wherein the swinging rod is protrudingly provided with a stopper against which a side of the lateral bearing lies.

3. The transmission mechanism of claim 2, wherein the position-limiting cover is penetrated by two fastening holes through which two screws can be inserted respectively so as to fix the position-limiting cover at a position adjacent to the motor.

* * * * *

UNITED STATES PATENT AND TRADEMARK OFFICE
CERTIFICATE OF CORRECTION

| | | |
|---|---|---|
| PATENT NO. | : 8,771,308 B2 | Page 1 of 1 |
| APPLICATION NO. | : 13/137089 | |
| DATED | : July 8, 2014 | |
| INVENTOR(S) | : Su-Lin Lin | |

It is certified that error appears in the above-identified patent and that said Letters Patent is hereby corrected as shown below:

On the title page

"Item (73) Assignee: Mei-Cha-Na Hsinyen Co., Ltd., Taipei (TW)"

should read:

--Item (73) Assignee: Mei-Chi-Na Hsinyen Co., Ltd., Taipei (TW)--

Signed and Sealed this
Thirteenth Day of October, 2015

Michelle K. Lee
*Director of the United States Patent and Trademark Office*